United States Patent
Arcot-Krishnamurthy et al.

(10) Patent No.: US 8,954,147 B2
(45) Date of Patent: Feb. 10, 2015

(54) TIMING FOR HIS-BUNDLE PACING

(75) Inventors: Shantha Arcot-Krishnamurthy, Vadnais Heights, MN (US); Allan C. Shuros, St. Paul, MN (US); Jiang Ding, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 569 days.

(21) Appl. No.: 13/277,617

(22) Filed: Oct. 20, 2011

(65) Prior Publication Data

US 2012/0101542 A1 Apr. 26, 2012

Related U.S. Application Data

(60) Provisional application No. 61/405,869, filed on Oct. 22, 2010.

(51) Int. Cl.
*A61N 1/365* (2006.01)
*A44C 15/00* (2006.01)

(52) U.S. Cl.
CPC ............... *A44C 15/00* (2013.01); *A61N 1/365* (2013.01)
USPC ........................................................ 607/25

(58) Field of Classification Search
CPC .................................................... A61N 1/365
USPC ........................................................ 607/25
See application file for complete search history.

(56) References Cited

U.S. PATENT DOCUMENTS

| | | | |
|---|---|---|---|
| 5,549,109 A | 8/1996 | Samson et al. | |
| 6,804,555 B2 | 10/2004 | Warkentin | |
| 7,245,973 B2 | 7/2007 | Liu et al. | |
| 7,512,440 B2 | 3/2009 | Ortega et al. | |
| 8,010,191 B2 | 8/2011 | Zhu et al. | |
| 8,014,861 B2 | 9/2011 | Zhu et al. | |
| 2003/0078625 A1 | 4/2003 | Casavant | |
| 2005/0149137 A1 | 7/2005 | Chinchoy et al. | |
| 2006/0064027 A1 | 3/2006 | Borowitz et al. | |
| 2006/0142812 A1 | 6/2006 | Ortega et al. | |
| 2007/0179546 A1 | 8/2007 | Yu et al. | |
| 2008/0319499 A1 | 12/2008 | Zhu et al. | |
| 2009/0005832 A1 | 1/2009 | Zhu et al. | |

FOREIGN PATENT DOCUMENTS

| | | |
|---|---|---|
| EP | 0450387 A2 | 10/1991 |
| WO | WO-2010/071849 A2 | 6/2010 |
| WO | WO-2012054713 A1 | 4/2012 |

OTHER PUBLICATIONS

"International Application Serial No. PCT/US2011/057078, International Search Report mailed Feb. 7, 2012", 5 pgs.
"International Application Serial No. PCT/US2011/057078, International Written Opinion mailed Feb. 7, 2012", 5 pgs.
"International Application Serial No. PCT/US2011/057078, International Preliminary Report on Patentability mailed May 2, 2013", 7 pgs.
"Japanese Application Serial No. 2013-535085, Office Action mailed Mar. 18, 2014", With English Translation, 7 pgs.

*Primary Examiner* — Mark W Bockelman
(74) *Attorney, Agent, or Firm* — Schwegman Lundberg & Woessner, P.A.

(57) ABSTRACT

An A-H delay can be specified, such as by computing the A-H delay using a measured cardiovascular physiologic parameter. The A-H delay can be used for specifying timing between a paced or sensed atrial contraction and a His-bundle pacing time.

9 Claims, 5 Drawing Sheets

TIMING FOR HIS-BUNDLE PACING

CROSS REFERENCE TO RELATED APPLICATIONS

This application claims benefit of priority under 35 U.S.C. 119(e) to Arcot-Krishnamurthy et al., U.S. Provisional Patent Application Ser. No. 61/405,869, entitled "TIMING FOR HIS-BUNDLE PACING", filed on Oct. 22, 2010, which is hereby incorporated herein by reference in its entirety.

BACKGROUND

Certain cardiac rhythm or function management devices can sense intrinsic heart contractions, deliver pacing pulses to evoke responsive heart contractions, or deliver a shock to interrupt certain arrhythmias. In certain examples, this can help improve a patient's heart rhythm or can help coordinate a spatial nature of a heart contraction, either of which can improve cardiac output of blood to help meet the patient's metabolic need for such cardiac output.

Dual chamber pacing can involve pacing the right atrium (RA), followed by a right ventricular (RV) pace, which is typically delivered at the RV apex. In an example, an atrioventricular (AV) delay between an RA pace or sensed RA contraction and a scheduled following RV pace can be set to optimize ventricular filling time, which, in turn can promote better cardiac output of blood. Cardiac resynchronization therapy (CRT) can be used to synchronize or spatially coordinate RV and left ventricular (LV) contractions, such as for more efficient pumping. CRT can involve using a coronary sinus (CS) lead to position one or more electrodes near the LV. CRT can include pacing both the RV apex and the LV (e.g., via the CS lead), such as to induce a simultaneous contraction of the RV and LV. However, such a technique can require a CS lead to access the LV. Right atrium (RA) or RV His-bundle pacing can be used instead of RV and CS/LV bi-ventricular pacing.

Ortega et al. U.S. Pat. No. 7,512,440, entitled VENTRICULAR PACING, refers to a method and apparatus for treating a condition of a patient's heart, including placing a first electrode and a second electrode in a right ventricle of the heart. Borowitz et al. U.S. Patent Publication No. 2006/0064027, entitled IMPLANTABLE MEDICAL DEVICE WITH HIS-PURKINJE ACTIVITY DETECTION, refers to using an atrial lead and a ventricular lead to acquire data and processing the data to indicate electrical timing with the His-bundle.

Overview

The conduction pathway of the heart originates in the sinoatrial (SA) node in the right atrium of the heart. When functioning properly, the SA node is the primary natural pacemaker of the heart, generating intrinsic electrical impulses or action potentials, triggering the atria to contract. From the SA node, the conduction pathway follows intermodal pathways to the atrioventricular (AV) node, located between the atrium and the ventricle. After the AV node, conduction continues through the His-bundle to the left and right bundle branches, then to the purkinje fibers, to the apex of the heart, and finally up and around to the ventricular myocardium.

The present inventors have recognized, among other things, that cardiac contractions utilizing the natural conduction pathway, such as intrinsic contractions, are generally advantageous over typical apical or biventricular pacing, providing a faster, more focused and efficient contraction. Accordingly, providing stimulation energy (e.g., a pacing energy) to a portion of the natural conduction pathway (e.g., the His-bundle, etc.) can utilize the faster conducting fibers (in contrast to slower activating muscle cells), providing more physiological stimulation and better hemodynamic benefits.

The present inventors have also recognized that, when providing pacing energy to the His-bundle, it can be advantageous to provide the stimulation energy at a time that is similar to the time when the intrinsic electrical energy would arrive at the His-bundle in a properly functioning heart. As such, it can be advantageous to provide pacing energy to the His-bundle at a time that is after a sensed atrial contraction but before the start of a ventricular contraction. The term "atrial-His-bundle (A-H) delay" can be used to refer to a specified timing between a paced or sensed atrial contraction and a scheduled His-bundle pacing time.

The present inventors have recognized, among other things, that the considerations for specifying a desired value of A-H delay can be different from atrial-ventricular (A-V) delay considerations. For example, the A-H delay value can be different from the A-V delay value because pacing at the His-bundle can take advantage of the faster natural conduction pathways of the heart in evoking a resulting ventricular contraction. Moreover, selecting a desired value of A-H delay can focus on helping increase or maximize ventricular filling. In contrast, the desired value of A-V delay will typically include require consideration of both intra-ventricular synchrony and ventricular filling, and therefore may not be capable of maximizing ventricular filling.

The present inventors have also recognized that using a conventional A-V delay value for the A-H delay for delivering His-bundle pacing may not work, or may not work as well as otherwise may be possible. For example, pacing energy, to be effective, should be delivered to the paced region before intrinsic electrical energy arrives at the region. A conventional A-V delay value may be longer than the A-H delay value, because electrical energy following the natural conduction pathway of the heart typically arrives at the His-bundle before arriving at the ventricular apex myocardium. A pace delivered at the His-bundle using a conventional A-V delay value may be ineffective because, after the A-V delay has elapsed, the intrinsic electrical energy may have already arrived at the His-bundle. Accordingly, the present inventors have developed, among other things, a technique for establishing an A-H delay for His-bundle pacing, such as a technique for RA His-bundle pacing or a technique for RV septal His-bundle pacing.

This document describes, among other things, an apparatus and method in which an atrial-His ("A-H") delay can be used, such as for specifying timing between a paced or sensed atrial contraction and a His-bundle pacing time.

Example 1 includes subject matter that can include an apparatus comprising: a timing circuit configured to receive a specified A-H delay, for use for specifying timing between a paced or sensed atrial contraction and a His-bundle pacing time, the specified A-H delay computed using a measured cardiovascular physiologic parameter; and an electrostimulation energy delivery control circuit configured to be communicatively coupled to the timing circuit and to provide a control signal to deliver, in response to a paced or sensed atrial contraction, and using the specified A-H delay, an electrostimulation at a location that is at or near the His-bundle.

In Example 2, the subject matter of Example 1 can optionally include the measured cardiovascular physiologic parameter comprising a P-wave duration of an electrical cardiac signal.

In Example 3, the subject matter of one or any combination of Examples 1-2 can optionally include the measured cardiovascular physiologic parameter comprising a S1 time of a heart sound signal.

In Example 4, the subject matter of one or any combination of Examples 1-3 can optionally include the measured cardiovascular physiologic parameter comprising a time of a peak of a left atrial pressure signal.

In Example 5, the subject matter of one or any combination of Examples 1-4 can optionally include the timing circuit configured to receive the measured cardiovascular physiologic parameter and compute the specified A-H delay using the received physiologic parameter.

In Example 6, the subject matter of one or any combination of Examples 1-5 can optionally include the measured cardiovascular physiologic parameter comprising a P-wave duration of an electrical cardiac signal, and wherein the timing circuit is configured such that computing the specified A-H delay comprises: using the P-wave duration; and using an offset time representative of a delay between the end of the P-wave and a beginning of a QRS complex.

In Example 7, the subject matter of one or any combination of Examples 1-6 can optionally include the timing circuit configured such that computing the specified A-H delay comprises using, when the paced or sensed atrial contraction is a paced atrial contraction, an A-pace offset time representative of an atrial pacing-atrial sensing differential conduction delay.

In Example 8, the subject matter of one or any combination of Examples 1-7 can optionally include the measured cardiovascular physiologic parameter comprising a S1 time of a heart sound signal, and wherein the timing circuit is configured such that computing the specified A-H delay comprises: using the S1 time; and using an offset time representative of a delay between the S1 time and the His-bundle pacing time.

In Example 9, the subject matter of one or any combination of Examples 1-8 can optionally include the timing circuit configured such that computing the specified A-H delay comprises using, when the paced or sensed atrial contraction is a paced atrial contraction, an A-pace offset time representative of an atrial pacing-atrial sensing differential conduction delay.

Example 10 can include, or can optionally be combined with the subject matter of one or any combination of Examples 1-9 to include subject matter (such as a method, a means for performing acts, or a machine-readable medium including instructions that, when performed by the machine, cause the machine to perform acts), comprising: receiving a specified A-H delay, for use for specifying timing between a paced or sensed atrial contraction and a His-bundle pacing time, the specified A-H delay computed using a measured cardiovascular physiologic parameter; and in response to a paced or sensed atrial contraction and using the specified A-H delay, triggering a control signal for delivering an electro-stimulation at a location that is at or near the His-bundle.

In Example 11, the subject matter of one or any combination of Examples 1-10 can optionally include the measured cardiovascular physiologic parameter comprising a P-wave duration of an electrical cardiac signal.

In Example 12, the subject matter of one or any combination of Examples 1-11 can optionally include the measured cardiovascular physiologic parameter comprising a S1 time of a heart sound signal.

In Example 13, the subject matter of one or any combination of Examples 1-12 can optionally include the measured cardiovascular physiologic parameter comprising a time of a peak of a left atrial pressure signal.

In Example 14, the subject matter of one or any combination of Examples 1-13 can optionally include receiving the measured cardiovascular physiologic parameter, and computing the specified A-H delay using the received physiologic parameter.

In Example 15, the subject matter of one or any combination of Examples 1-14 can optionally include the measured cardiovascular physiologic parameter comprising a P-wave duration of an electrical cardiac signal, and wherein computing the specified A-H delay comprises: using the P-wave duration; and using an offset time representative of a delay between the end of the P-wave and a beginning of a QRS complex.

In Example 16, the subject matter of one or any combination of Examples 1-15 can optionally include computing the specified A-H delay comprising using, when the paced or sensed atrial contraction is a paced atrial contraction, an A-pace offset time representative of an atrial pacing-atrial sensing differential conduction delay.

In Example 17, the subject matter of one or any combination of Examples 1-16 can optionally include the measured cardiovascular physiologic parameter comprising a S1 time of a heart sound signal, and wherein computing the specified A-H delay comprises: using the S1 time; and using an offset time representative of a delay between the S1 time and the His-bundle pacing time.

In Example 18, the subject matter of one or any combination of Examples 1-17 can optionally include computing the specified A-H delay comprising using, when the paced or sensed atrial contraction is a paced atrial contraction, an A-pace offset time representative of an atrial pacing-atrial sensing differential conduction delay.

Example 19 can include, or can optionally be combined with the subject matter of one or any combination of Examples 1-18 to include subject matter (such as a method, a means for performing acts, or a machine-readable medium including instructions that, when performed by the machine, cause the machine to perform acts), comprising: receiving a specified A-H delay, for use for specifying timing between a paced or sensed atrial contraction and a His-bundle pacing time, the specified A-H delay computed using a measured cardiovascular physiologic parameter; and in response to a paced or sensed atrial contraction and using the specified A-H delay, triggering a control signal for delivering an electro-stimulation at a location that is at or near the His-bundle.

In Example 20, the subject matter of one or any combination of Examples 1-19 can optionally include the measured cardiovascular physiologic parameter comprising a P-wave duration of an electrical cardiac signal.

In Example 21, the subject matter of one or any combination of Examples 1-20 can optionally include the measured cardiovascular physiologic parameter comprising a S1 time of a heart sound signal.

In Example 22, the subject matter of one or any combination of Examples 1-21 can optionally include the measured cardiovascular physiologic parameter comprising a time of a peak of a left atrial pressure signal.

In Example 23, the subject matter of one or any combination of Examples 1-22 can optionally include receiving the measured cardiovascular physiologic parameter, and computing the specified A-H delay using the received physiologic parameter.

In Example 24, the subject matter of one or any combination of Examples 1-23 can optionally include the measured cardiovascular physiologic parameter comprising a P-wave duration of an electrical cardiac signal, and wherein computing the specified A-H delay comprises: using the P-wave duration; and using an offset time representative of a delay between the end of the P-wave and a beginning of a QRS complex.

In Example 25, the subject matter of one or any combination of Examples 1-24 can optionally include computing the specified A-H delay comprising using, when the paced or sensed atrial contraction is a paced atrial contraction, an A-pace offset time representative of an atrial pacing-atrial sensing differential conduction delay.

In Example 26, the subject matter of one or any combination of Examples 1-25 can optionally include the measured cardiovascular physiologic parameter comprising a S1 time of a heart sound signal, and wherein computing the specified A-H delay comprises: using the S1 time; and using an offset time representative of a delay between the S1 time and the His-bundle pacing time.

In Example 27, the subject matter of one or any combination of Examples 1-26 can optionally include computing the specified A-H delay comprising using, when the paced or sensed atrial contraction is a paced atrial contraction, an A-pace offset time representative of an atrial pacing-atrial sensing differential conduction delay.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, an apparatus and method in which an atrial-His ("A-H") delay can be used, such as for specifying timing between a paced or sensed atrial contraction and a His-bundle pacing time.

Figure 1:
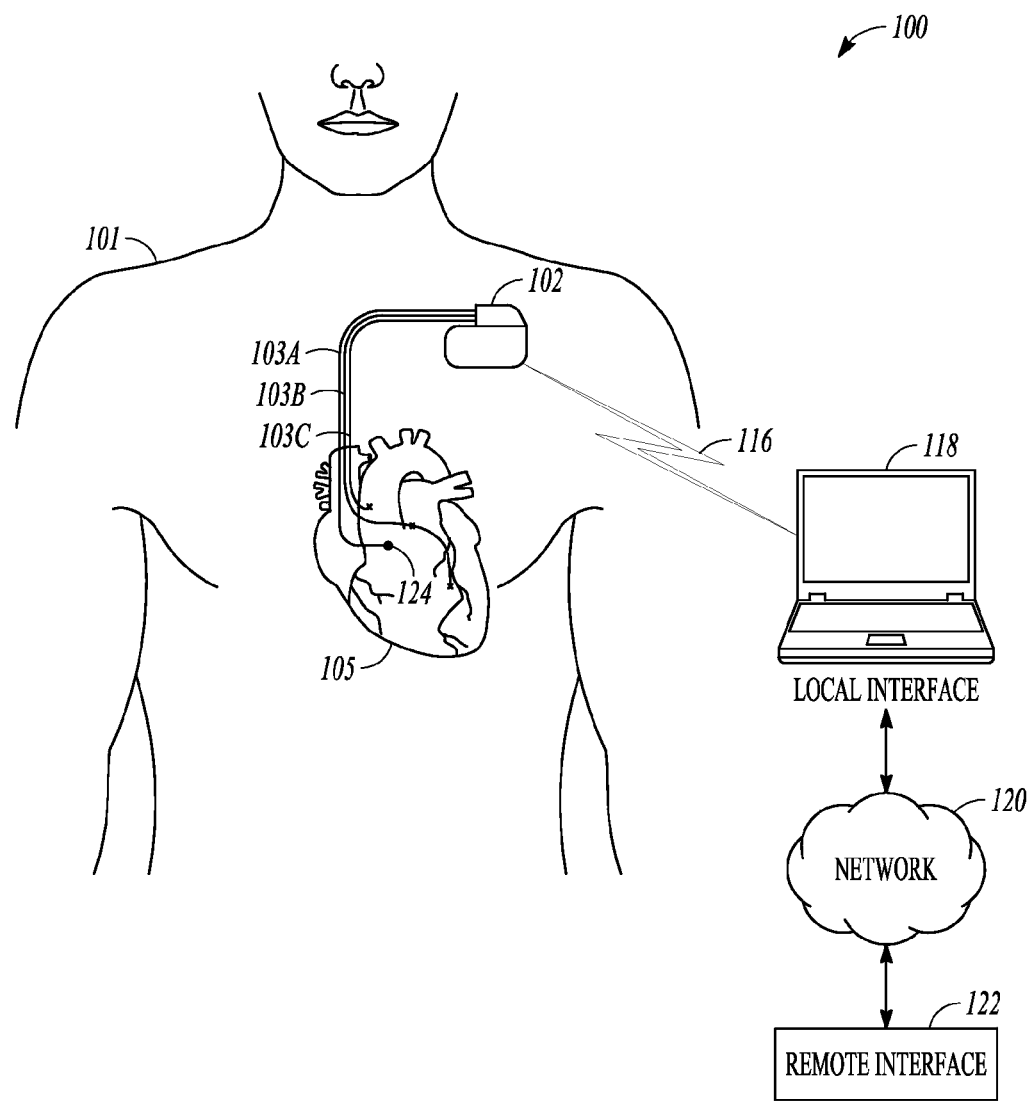
FIG. 1 illustrates an example of portions of an apparatus that can enable specifying and using an A-H delay.

FIG. 1 illustrates an example of portions of an apparatus 100 such as can be used for specifying and using the A-H delay. In the example of FIG. 1, an ambulatory medical device, such as an implantable medical device (IMD) 102 can be configured to monitor or provide therapy to a patient 101. In an example, an ambulatory medical device can include an external (e.g., wearable) medical device or an implantable medical device, among others. For example, ambulatory medical devices can include one or more of a pacemaker, an implantable cardioverter defibrillator (ICD), a cardiac resynchronization therapy pacemaker (CRT-P), a cardiac resynchronization therapy defibrillator (CRT-D), a pulmonary artery (PA) pressure sensor, a neurostimulation device, a physiological signals monitor, a cardiovascular monitor, a stent, a drug pump, or the like. In an example, the IMD 102 can be configured to sense physiological data, derive a physiological measure or correlation, or store data such as for later communication or reference. Examples of physiological data can include implantable electrograms, surface electrocardiograms, heart rate intervals (e.g., AA, VV, AV or VA intervals), electrogram templates such as for tachyarrhythmia discrimination, pressure (e.g., intracardiac or arterial pressure), oxygen saturation, activity, heart rate variability, heart sounds, impedance, respiration, posture, intrinsic depolarization amplitude, or the like. More than one IMD 102 may be implanted. For example, medical devices that have specific functions can be placed in accordance with their function. In addition, the IMD 102 can be composed of more than one device, with each device having one or more functions. Similarly, the position of the IMD 102 can vary. Examples of other locations can include the patient's abdomen, back, arm, or the like.

In an example, the IMD 102 can include or can be coupled to one or more electrodes, such as which can be carried by one or more leads. Such leads can include one or more intracardiac leads 103A-C, which can be implanted in a human body with portions of the intracardiac leads 103A-C inserted into the heart 105. The intracardiac leads 103A-C can include one or more electrodes, positionable within the heart 105, configured to sense electrical activity of the heart 105, or to deliver electrical stimulation energy to the heart 105. In an example, one or more of the intracardiac leads 103A-C can be configured to deliver pacing pulses to treat various arrhythmias. One or more of the intracardiac leads 103A-C can be configured to deliver pacing pulses or defibrillation shocks, such as to treat one or various arrhythmias. The IMD 102 can include one or more extracardiac leads, such as subcutaneous leads, subpectoral leads, and epicardial leads. In an example, one or more of the intracardiac leads 103A-C can be positioned at a location 124 that is at or near the His-bundle, such as is illustrated by the lead 103A in the example of FIG. 1.

In an example, the IMD 102 can be configured to be capable of communication, such as bidirectional communication using a connection 116 with an external or other local interface 118. Examples of the connection 116 can include wireless telemetry, such as inductive, radio frequency (RF), blue tooth, infrared, or one or more other communication connections. A local interface 118 can be a device configured such as to receive input, process instructions, store data, present data in a human-readable form, or communicate with other devices. The IMD 102 can be configured to receive commands from the local interface 118 or to communicate one or more patient indications to the local interface 118. Examples of patient indications can include one or more sensed or derived measurements such as heart rate, heart rate variability, heart sounds, data related to ischemia events, data related to tachyarrhythmia episodes, hemodynamics and hemodynamic stability, respiration, cardiac motion, cardiac contractility, cardiac output, patient activity, therapy history, autonomic balance, motor trends, electrogram templates for tachyarrhythmia discrimination, heart rate variability trends or templates, or trends, templates, or abstractions derived from sensed physiological data. Patient indications can include or be derived from one or more physiological indications, such as the physiological data described above. The IMD 102 can also be configured to communicate one or more device indications to the local interface 118. Examples of device indications can include lead/shock impedance, pacing amplitudes, pacing capture thresholds, or one or more other device metrics. In an example, the IMD 102 can be configured to communicate sensed physiological signal data to the local interface 118, which can then communicate the signal data to a remote device such as for processing. In an example, when more than one IMD 102 has been employed, the multiple IMD 102 devices can be configured to communicate with each other, such as by using the connection 116.

In an example, the local interface 118 can be located in close proximity to the patient 101. The local interface 118 can be attached, coupled, integrated or incorporated with a personal computer or a specialized device, such as a medical device programmer. In an example, the local interface 118 can be a hand-held device, such as a personal digital assistant (PDA) or smart phone. In examples, the local interface 118 can be a specialized device or a personal computer. In an example, the local interface 118 can be adapted to communicate with a remote interface 122. Examples of a remote interface can include a remote computer or server or the like. The communication link between the local interface 118 and the remote interface 122 can be made through a computer or telecommunications network 120. The network 120 can include, in various examples, one or more wired or wireless networking such as the Internet, satellite telemetry, cellular or other mobile telephone telemetry, microwave telemetry, or using one or more other long-range communication networks.

Figure 2:
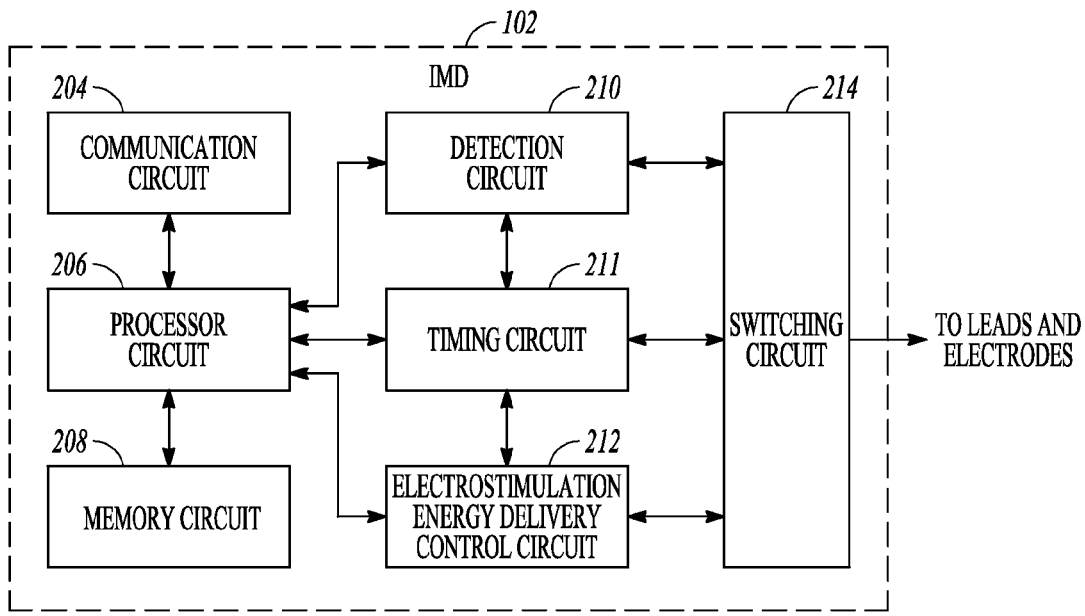
FIG. 2 illustrates an example of portions of an implanted medical device.

FIG. 2 illustrates an example of portions of the IMD 102. In the example of FIG. 2, the IMD 102 can include a switching circuit 214, such as for selectively connecting to one or more of the various sensors, such as can be located on the leads 103A-C or elsewhere. In an example, a detection circuit 210 can be selectively coupled to various sensors, such as by the switching circuit 214. In an example, the detection circuit 210 can include one or more sense amplifiers, filter circuits, analog-to-digital converters, level-detection circuits, or other circuits such as for sensing or signal-processing one or more signals, such as cardiac signals.

In an example, a timing circuit 211 can be configured to receive a specified A-H delay. The A-H delay can be used such as for specifying timing between a paced or sensed atrial contraction and a His-bundle pacing time, such as is explained further below.

In an example, the timing circuit 211 can be configured to receive one or more cardiovascular physiologic parameters using one or more physiologic sensors. Examples of sensors that can be used to receive the one or more cardiovascular physiologic parameters can include, but are not limited to, one or more of: an electrical cardiac signal sensing circuit, a heart sounds sensor, a transthoracic impedance measurement circuit, an intracardiac impedance measurement circuit, an accelerometer, a blood pressure sensor, a wall motion sensor, a heart rate variability sensor, or a physical activity sensor. In an example, the timing circuit can be configured to compute the A-H delay using the received cardiovascular physiologic parameter, such as is explained further below.

In an example, an electrostimulation energy delivery control circuit 212 can be selectively coupled to various sensors, such as by the switching circuit 214. The electrostimulation energy delivery control circuit 212 can include therapy energy generation circuitry (e.g., capacitive, inductive, or other) such as for generating, storing, or delivering an electrostimulation, cardioversion, defibrillation, drug delivery, or other energy.

In an example, the detection circuit 210, the timing circuit 211, or the electrostimulation energy delivery control circuit 212 can be coupled to a processor circuit 206. The processor circuit 206 can perform instructions, such as for signal processing of signals derived by the timing circuit 210, or for controlling operation of the electrostimulation energy delivery control circuit 212, or for controlling one or more other operations of the IMD 102.

In an example, the processor circuit 206 can be coupled to or include a memory circuit 208, such as for storing or retrieving instructions or data. The processor circuit 206 can be coupled to or include a communication circuit 204, such as for communicating with another location, such as with the local interface 118. In an example, the IMD 102 can include multiple processor circuits 206. One or more processor circuits can be included in one or more of the IMD 102, the local interface 118, or the remote interface 122, such as for distributing the processing load, such as for decreasing the power consumption of the IMD 102.

Figure 3:
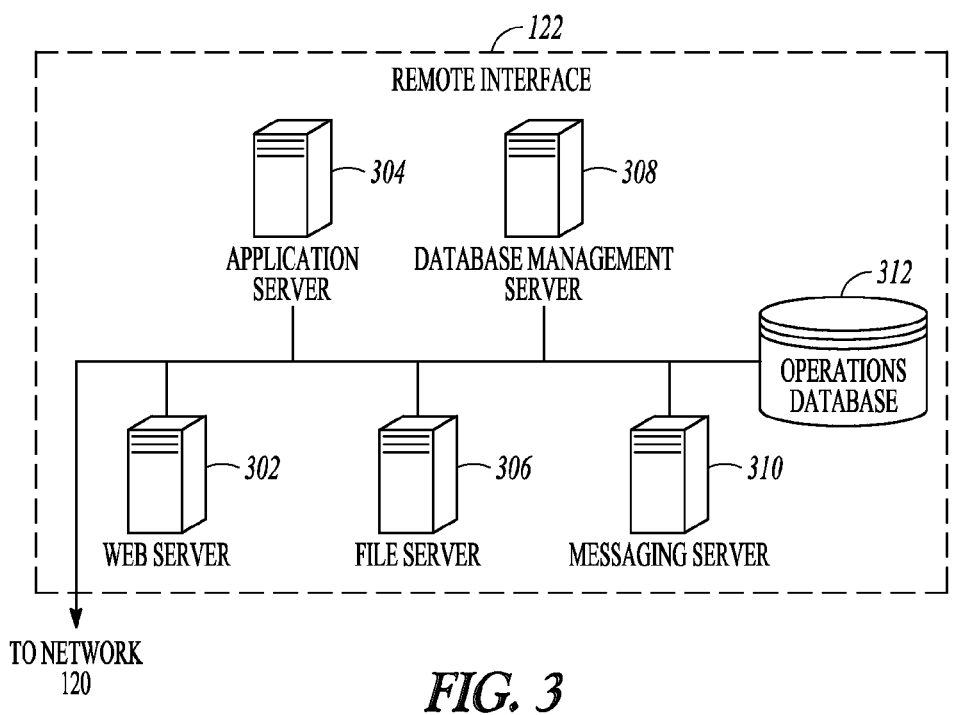
FIG. 3 illustrates an example of portions of a remote interface that can enable specifying and using an A-H delay.

FIG. 3 illustrates an example of the remote interface 122. In an example, the remote interface 122 can include one or more computers, such as a database management server 308, a messaging server 310, a file server 306, an application server 304, or a web server 302. The database management server 308 can be configured to provide one or more database services to one or more clients, which can include one or more other servers, such as in the remote interface 122. The messaging server 310 can be configured to provide a communication platform for one or more users of the remote interface 122. For example, the messaging server 310 can provide an email communication platform. Examples of other types of messaging can include one or more of short message service (SMS), instant messaging, or paging services. The file server 306 can be used to store patient data, device data, documents, images, and other files for the web server 302 or as a general document repository. The application server 304 can provide one or more applications to the web server 302. To enable some of these services provided by these servers 302, 304, 306, 308, and 310, the remote interface 122 can include an operations database 312. The operations database 312 can be used for various functions and can be composed of one or more logically or physically distinct databases. The operations database 312 can be used to store clinical data such as for individual patients, one or more patient populations, one or more patient trials, or the like. In an example, the operations database 312 can be used to store patient data such as for individual patients, one or more patient populations, one or more patient trials, or the like. For example, the operations database 312 can include a copy of, a portion of, a summary of, or other data from an electronic medical records (EMR) system. In an example, the operations database 312 can store device information, such as one or more device settings such as for a particular patient or a group of patients, one or more preferred device settings such as for a particular clinician or a group of clinicians, device manufacturer information, or the like. In an example, the operations database 312 can be used to store raw, intermediate, or summary data such as of one or more patient indications, for example, along with one or more probabilistic outcomes (e.g., a patient population profile and a corresponding 1-year survival curve).

Figure 4:
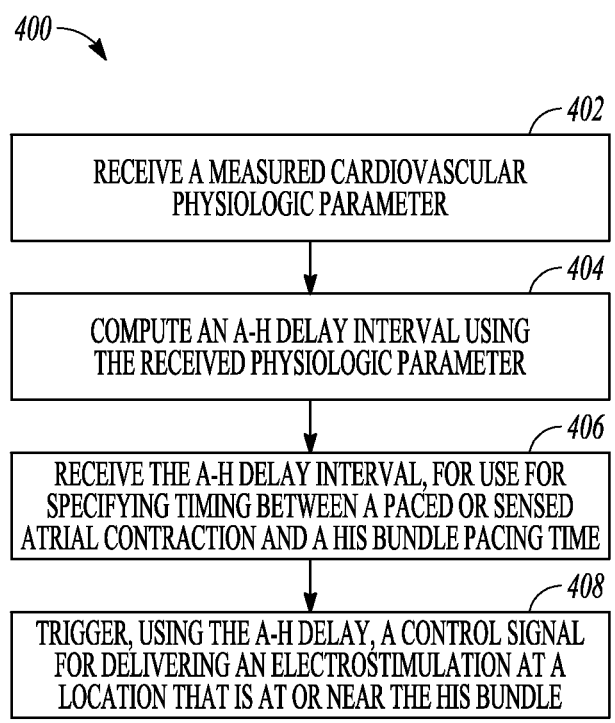
FIG. 4 illustrates an example of a technique for computing an A-H delay using a received physiologic parameter, using the A-H delay for specifying timing between a paced or sensed atrial contraction and a His-bundle pacing time, and triggering, using the A-H delay, a control signal for delivering an electrostimulation at a location that is at or near the His-bundle.

FIG. 4 is a diagram illustrating an example of a technique 400 for computing an A-H delay.

At 402, a measured cardiovascular physiologic parameter can be received. Examples of cardiovascular physiologic parameters include one or more of an implantable electrogram, surface electrocardiogram, measured heart rate intervals (e.g., AA, VV, AV or VA intervals), pressure (e.g., intracardiac or arterial pressure), heart sounds, cardiac impedance, or intrinsic depolarization amplitude.

At 404, an A-H delay, for use for specifying timing between a paced or sensed atrial contraction and a His-bundle pacing time, can be computed using the received physiologic parameter. For example, the A-H delay can be computed such as by using an electrical cardiac signal such as one or more of an implantable electrogram or surface electrocardiogram signal.

Figure 5A:
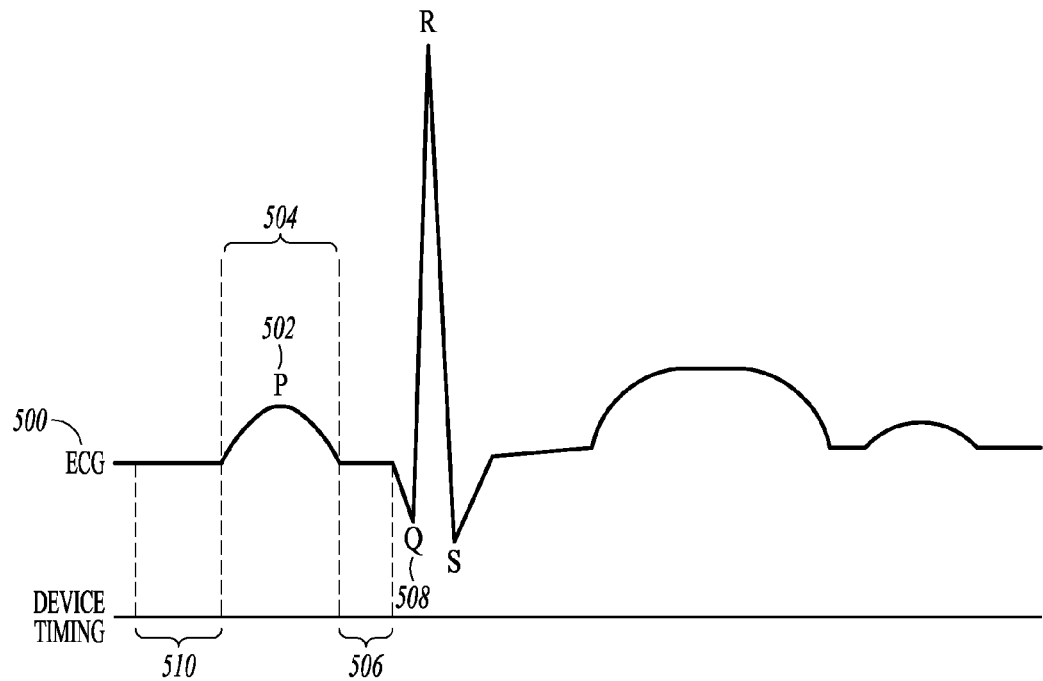
FIG. 5A is an illustration of an ECG signal.

Referring to FIG. 5A, an electrocardiogram (ECG) signal 500 is illustrated. A P-wave 502 can be representative of the electrical activation of the atrium. A duration 504 can be representative of the duration of the P-wave 502. An onset of the Q-wave 508 can signify the beginning of the right ventricular activation. An offset 506 can be a device parameter representative of a delay between the end of the P-wave 502 and the beginning of the Q-wave 508.

The ECG signal 500 can be obtained from an external or internal sensor. For example, the ECG signal 500 can be obtained such as by a noninvasive recording produced by an electrocardiographic device that implements one or more skin electrodes. In an example, the ECG signal 500 can be obtained from an implanted device, such as the IMD 102. For example, the ECG signal 500 can be obtained using subcutaneous electrodes or intracardiac leads, such as the leads 103A-C. Examples of locations of the intracardiac leads can include the floor of the right atrium (RA), the septal region, or the coronary sinus. In an example, the ECG signal 500 can be obtained using an electrode on a lead located in the right atrium in a unipolar sensing mode and using the housing of the IMD 102 as a can electrode. In an example, the ECG signal 500 can be obtained using two electrodes located at the housing of the IMD 102.

In an example, the ECG signal 500 can represent a composite signal, such as can be obtained using averaged signals. For example, multiple cardiac cycles can be captured by the electrocardiographic device and aligned using morphological analysis. Abnormal or anomalous signals can be discarded to obtain a good representation of an average signal. In addition, the signals can be upsampled such as to provide additional resolution.

In an example, the ECG signal 500 can represent one or more ECG signals obtained from the patient 101. In an example, the ECG signal 500 can represent an average signal from multiple patients. For example, the ECG signal 500 can be selected from an average ECG signal of a patient population with similar characteristics to the patient 101. Examples of patient characteristics can include, but are not limited to, one or more of the patient's age, gender, ethnicity, left ventricular ejection fraction (LVEF), New York Heart Association (NYHA) heart failure classification, results of a six-minute walk test (6MW), quality of life, heart failure etiology, body mass index (BMI), blood pressure, medication, co-morbidity, arrhythmia history, implant history, or geographic location.

In an example, the A-H delay can be computed such as by using the measured P-wave duration 504 and the measured offset 506. For example, the A-H delay can be computed such as by summing the P-wave duration 504 and the offset 506.

In an example, the P-wave duration 504 can be determined such as by a review of the ECG signal 500. The review can include an estimate of the P-wave duration 504 and can be performed by one or more of a clinician, a caregiver, or other. In an example, the P-wave duration 504 can be determined such as by the IMD 102. For example, the IMD 102 can capture one or more P-waves from the patient 101 over time. The P-wave duration 504 can be determined by the device automatically such as by using the one or more P-waves captured by the IMD 102. This can include a morphological analysis of the one or more captured P-waves to determine their respective durations, such as by using a level detector circuit to detect an onset of the P-wave and cessation of the P-wave and a timer circuit to measure a time interval between the two. The P-wave duration 504 can be determined using the one or more durations of the captured P-waves, such as by assigning the value of the P-wave duration 504 using a mean, median, or other central tendency value of the durations of the one or more captured P-waves.

In an example, the P-wave duration 504 can be determined on a recurring basis, such as by the IMD 102 or by a clinician, a caregiver, or other. Examples of such a recurring basis can include, but are not limited to: beat-to-beat, hourly, daily, weekly, monthly, yearly, at each patient checkup, or at each review of patient data.

In an example, the offset 506 can be determined using the ECG signal 500. For example, similar to the determination of the P-wave duration 504, the offset 506 can be determined such as by reviewing the ECG signal 500. The review can include an estimate of the offset 506 and can be performed by one or more of a clinician, a caregiver, or other.

In an example, the offset 506 can be assigned a nominal value, such as a value representing a time that is between zero and fifty milliseconds. For example, the offset 506 can be assigned a nominal value of ten milliseconds. In an example, the offset 506 can be assigned a value corresponding to a patient population. The offset 506 can be selected from a patient population using the characteristics of the patient 101, such as the characteristics described above.

In an example, the offset 506 can be determined automatically such as by the IMD 102. For example, the IMD 102 can capture one or more ECG signals over time from the patient 101. The offset 506 can be determined such as by using the one or more signals captured by the IMD 102. This can include a morphological analysis of the one or more captured signals to estimate the durations from the end of the P-waves to the beginning of the QRS complexes. This can involve using a level detector circuit to detect the cessation of the P-wave and a level detector circuit to detect the beginning of the QRS complex, and a timer circuit to measure a time interval between the two. The offset 506 can be determined using one or more such durations, such as by assigning the value of the offset 506 using a mean, median, or other central tendency value of the measured durations. The offset 506 can change based on the location of the RA lead position. If the RA lead is positioned lower in the atrium (e.g., the floor of the RA) the atrial activation can be sensed at a time that is closer to the beginning of the ventricular activation. In such an example, the offset 506 can be smaller in magnitude than if the RA lead is positioned higher in the atrium (e.g., the septal region).

In an example, the offset 506 can be assigned a value using the hemodynamic response of the patient 101 to an electrostimulation delivered at the location 124 that is at or near the His-bundle. In an example, the cardiac contractility of the patient 101 can be monitored as an indication of the strength of a cardiac contraction. For example, the rate of change of intra-chamber blood pressure (dP/dt) can be monitored, such as by using a cardiac impedance sensor. The monitored dP/dt can be used as a proxy to indicate the left ventricular contraction strength of the patient 101. Electrostimulation energy can be delivered at or about the His-bundle using varying offset values, and a hemodynamic response variable (e.g., dP/dt) can be monitored. Based on such testing, the offset 506 can be assigned a value that produces a maximum magnitude of dP/dt in response to the delivered electrostimulation, indicating a stronger contraction for the corresponding value of the offset. In an example, the cardiac impedance of the patient 101 in response to an electrostimulation delivered at the location 124 that is at or near the His-bundle can be monitored, such as by using a cardiac impedance sensor. Electrostimulation energy can be delivered at or about the His-bundle using varying offset values and a hemodynamic response variable (e.g., cardiac impedance) can be monitored. Based on such testing, the offset 506 can be assigned a value that produces a maximum rate of decrease of cardiac impedance during a cardiac contraction, indicating a stronger contraction for the corresponding value of the offset. In an example, an indication of the cardiac output of the patient 101 can be monitored, such as by measuring the pulse pressure or left ventricular ejection fraction (LVEF) of the patient 101. For example, the cardiac output can be monitored, such as by using a pulmonary artery pressure sensor or a cardiac impedance sensor. Electrostimulation energy can be delivered at or about the His-bundle using varying offset values and a hemodynamic response variable (e.g., indicative of pulse pressure or LVEF) can be monitored. The offset 506 can be assigned a value that produces a maximum cardiac output in response to the delivered electrostimulation.

In an example, the offset 506 can be assigned a value using a technique to verify capture of the His-bundle in response to an electrostimulation delivered at the location 124 that is at or near the His-bundle. For example, the electrostimulation energy can be delivered at or about the His-bundle using varying offset values, such as by using offset values determined to produce a desired hemodynamic response, such as is described above. In an example, electrical cardiac signals can be monitored to determine if a response indicative of His-bundle capture is present, such as described or incorporated by reference in Dong et al., U.S. Provisional Patent Application Ser. No. 61/328,248, entitled "HIS-BUNDLE CAPTURE VERIFICATION AND MONITORING," filed May 6, 2010, which is incorporated herein by reference in its entirety, including its description of capture determination.

In an example, the offset 506 can be determined using a non-recurring technique. For example, electrostimulation energy can be delivered using varying offset values. The offset 506 can be determined, such as by selecting the optimum offset value from the varying offset values, such as by using the hemodynamic response of the patient 101 as is described above. This can include a review by one or more of a clinician, a caregiver or other. Similarly, the selection of the optimum offset value can be determined such as by the IMD 102, such as by using the hemodynamic response of the patient 101.

In an example, the offset 506 can be determined on a recurring basis, such as by the IMD 102 or by a clinician, a caregiver, or other. Examples of such a recurring basis can include, but are not limited to: beat-to-beat, hourly, daily, weekly, monthly, yearly, at each patient checkup, or at each review of patient data.

In an example, if the atrial contraction is a paced atrial contraction, the A-H delay can be computed using an A-pace offset 510, such as by summing the P-wave duration 504, the offset 506, and the A-pace offset 510. The A-pace offset 510 can represent a differential conduction delay between atrial pacing and atrial sensing. For example, if the atrial contraction is induced by an atrial pace, the delivered pacing energy can take time to propagate from the pacing electrode to the SA node. The A-pace offset 510 can represent the propagation time from the pacing electrode to the SA node. In an example, if paced atrial contractions are induced at a rate that is greater than the body's metabolic demands, the propagation time of the electrical energy following the intermodal pathways to the atrioventricular (AV) node can increase. In such case, the P-wave duration 504 can increase. The A-pace offset 510 can represent the increased P-wave duration induced by the atrial pacing.

The A-pace offset 510, similar to the offset 506, can be assigned a nominal value, such as a value representing a time that is between thirty and seventy milliseconds. For example, the A-pace offset 510 can be assigned a nominal value of 30 milliseconds. In an example, the A-pace offset 510 can be assigned a value corresponding to a patient population, such as is described above in the discussion relating to the offset 506. The A-pace offset 510 can be determined such as by the IMD 102. For example, the IMD 102 can capture one or more ECG signals over time indicative of a cardiac contraction from the patient 101. The A-pace offset 510 can be determined using the one or more ECG signals. This can include a timing and morphological analysis of the one or more signals to determine the duration between the pacing time and the time of the start of the P-wave. The A-pace offset 510 can be determined using the one or more durations, such as by assigning the value of the A-pace offset 510 using a mean, median, or other central tendency value of the durations. In an example, the A-pace offset 510 can be assigned a value using the hemodynamic response of the patient 101 to an electrostimulation delivered at the location 124 that is at or near the His-bundle, such as is described above in the discussion relating to the offset 506. Similarly, the A-pace offset 510 can be assigned a value using His-bundle capture verification, using a non-recurring technique, or on a recurring basis.

Figure 5B:
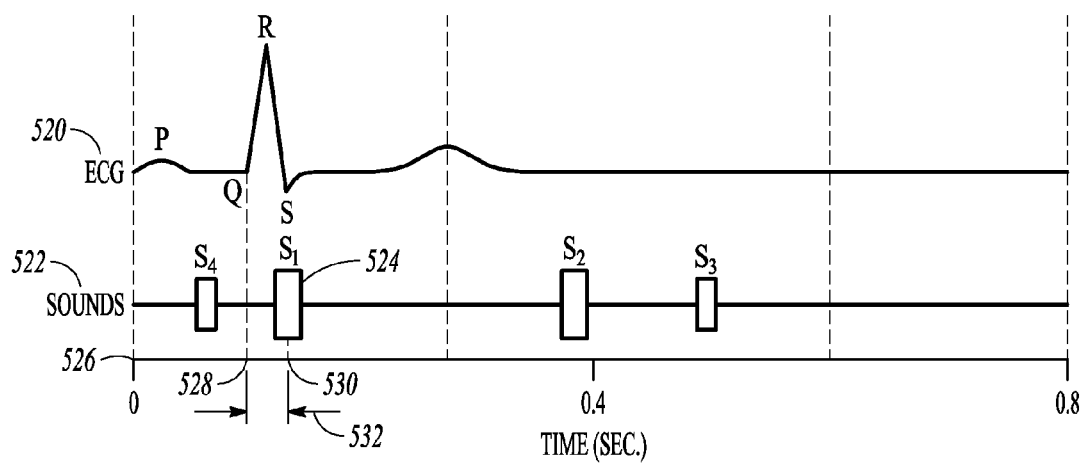
FIG. 5B is an illustration of an ECG signal and an associated heart sounds signal.

Referring to FIG. 5B, an electrocardiogram (ECG) signal 520 is illustrated along with an associated heart sounds signal 522. Heart sounds are associated with mechanical vibrations from activity of a patient's heart and the flow of blood through the heart. Heart sounds recur with each cardiac cycle and are separated and classified according to the activity associated with the vibration. The first heart sound (S1) 524 is the vibrational sound made by the heart during tensing of the mitral valve. The second heart sound (S2) marks the beginning of diastole. The third heart sound (S3) and fourth heart sound (S4) are related to filling pressures of the left ventricle during diastole. As is discussed above, the P-wave of the ECG signal 520 can be representative of the electrical activation of the atrium. A P-wave onset time 526 can represent the onset of the electrical activation of the atrium. A Q-wave onset time 528 can signify the beginning of the right ventricular action. An S1 heart sound time 530 can represent the end of the ventricular action. An offset 532 can be representative of a time between the start of the ventricular action and the S1 heart sound time 530.

The S1 heart sounds signal 522 can be obtained using an implantable or external heart sounds sensor, such as an acoustic sensor or accelerometer. In an example, the heart sounds signal 522 can represent averaged signals. For example, multiple cardiac cycles can be captured by the heart sounds sensor and aligned using morphological analysis. Abnormal or anomalous signals can be discarded to obtain a good representation of an average signal. In addition, the signals can be upsampled such as to provide additional resolution.

In an example, the heart sounds signal 522 can represent one or more heart sounds signals obtained from the patient 101. In an example, the heart sounds signal 522 can represent an average signal from multiple patients. For example, the heart sounds signal 522 can be selected from an average heart sounds signal of a patient population with similar characteristics to the patient 101, such as the characteristics described above.

In an example, the A-H delay can be computed using the S1 heart sound time 530 and the offset 532. For example, the A-H delay can be computed such as by subtracting the offset 532 from the S1 heart sound time 530. The offset 532 can be assigned a value using techniques such as those discussed above in the discussion relating to the offset 506 (FIG. 5A). This can include: a review of the ECG signal 520 and the heart sounds signal 522, such as by a clinician, a caregiver, or other, such as to determine the time between the S1 heart sound time 530 and the Q-wave onset time 528, assigning the offset 532 a nominal value such as by using a patient population with similar characteristics to the patient 101, assigning the offset 532 a value using the IMD 102 such as by using a morphological and timing analysis, assigning the offset 532 a value using the hemodynamic response of the patient 101 such as by using one or more of the cardiac contractility or cardiac output of the patient 101, assigning the offset 532 a value using information indicative of His-bundle capture verification, or assigning the offset 532 a value using an open loop technique or on a recurring basis.

In an example, if the atrial contraction is a paced atrial contraction, the A-H delay can be computed using the A-pace offset 510 (FIG. 5A), such as by summing the A-pace offset with the S1 heart sound time 530.

Figure 5C:
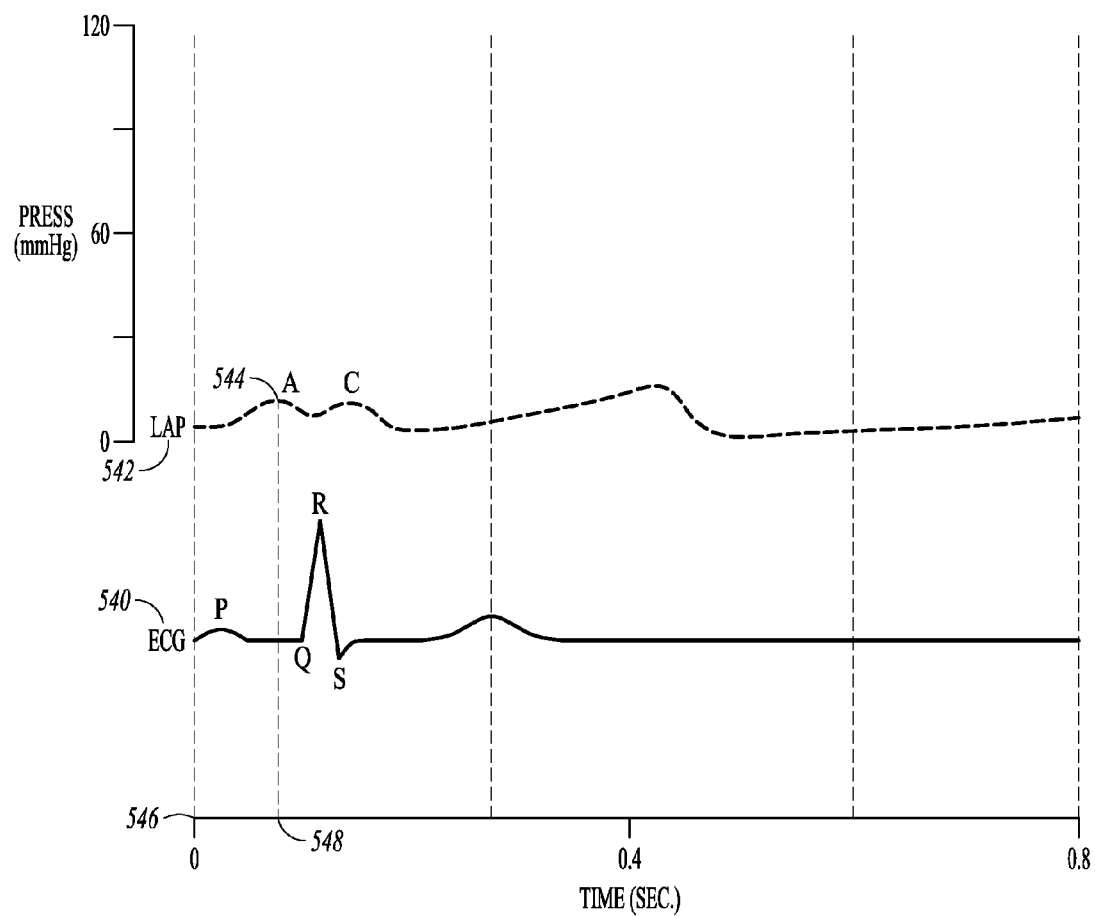
FIG. 5C is an illustration of an ECG signal and an associated left atrial pressure signal.

Referring to FIG. 5C, an electrocardiogram (ECG) signal 540 is illustrated along with an associated left atrial pressure (LAP) signal 542. The P-wave of the ECG signal 540 can be representative of the electrical activation of the atrium. A P-wave onset time 546 can represent the onset of the electrical activation of the atrium. The contraction of the atrium causes a rise in pressure in the atria, which is illustrated by the a-wave of the LAP signal 542. The QRS complex of the ECG signal 540 can be representative of the electrical activation of the ventricles. Ventricular contraction causes a rise in ventricular pressure. The A-V valves close when the ventricular pressure surpasses the atrial pressure. The closure of the A-V valves can cause a rise in pressure in the atria, which is illustrated by the c-wave of the LAP signal 542. A peak pressure 544 of the a-wave can represent a peak pressure in the atria during an atrial contraction. A peak pressure time 548 can represent the time of the peak pressure of the atria during the atrial contraction.

In an example, the LAP signal 542 can represent averaged signals. For example, multiple cardiac cycles can be captured and aligned using morphological analysis. Abnormal or anomalous signals can be discarded to obtain a good representation of an average signal. In addition, the signals can be upsampled such as to provide additional resolution.

In an example, the A-H delay can be computed using the LAP peak pressure time 548, such as by setting the A-H delay equal to the peak pressure time 548. In an example, the LAP signal 542 can represent one or more LAP signals obtained from the patient 101. In an example, the LAP signal 542 can represent an average signal from multiple patients. For example, the LAP signal 542 can be selected from an average LAP signal of a patient population with similar characteristics to the patient 101, such as the characteristics described above.

In an example, the peak pressure 544 and the peak pressure time 548 can be detected, such as by a review of the LAP signal 542 by a clinician, a caregiver, or other. In an example, the peak pressure 544 and the peak pressure time 548 can be detected, such as by the IMD 102, such as by using a morphological and timing analysis.

In an example, the A-H delay can be computed using information from one or more heart rate sensors. For example, the A-H delay can be shortened as the patient's heart rate increases, or can be lengthened as the patient's heart rate decreases. In an example, the A-H delay can be computed using information from one or more physical activity sensors. For example, the A-H delay can be shortened as the patient's physical activity increases, or can be lengthened as the patient's physical activity decreases. Either or both of the one or more heart rate sensors or one or more physical activity sensors can be used in the calculation of the A-H delay on a recurring basis, such as a beat-by-beat basis, once a second, once a minute, or the like. For example, the patient's heart rate can be continuously monitored. The computed A-H delay can be shortened if the patient's heart rate increases by a threshold amount, or increases at a rate that is greater than a threshold value. Similarly, the computed A-H delay can be lengthened if the patient's heart rate decreases by a threshold amount, or decreases by more than a threshold rate. Similar logic can apply to the patient's measured physical activity. In an example, if the patient's physical activity increases by more than a threshold amount, or increases by greater than a threshold rate, the A-H delay can be shortened. If the patient's physical activity decreases by more than a threshold amount, or decreases by more than a threshold rate, the A-H delay can be lengthened.

Referring again to FIG. 4, at 406 the A-H delay can be received, for use for specifying timing between a paced or sensed atrial contraction and a His-bundle pacing time. In an example, the A-H delay can be received such as by the IMD 102, such as by using the communication circuit 204. For example, if the A-H delay has been computed by a clinician, a caregiver, a remote device, or other, the A-H delay can be communicated to the IMD 102 such as by using one or more of the remote interface 122 or the local interface 118.

In an example, the A-H delay can be received by the timing circuit 211, such as from the communication circuit 204 or the processor circuit 206. For example, if the A-H delay has been received by the communication circuit 204, the A-H delay can be communicated to the timing circuit such as by using communication pathways of the IMD 102 such as those illustrated in FIG. 2. If the A-H delay has been computed such as by the processor circuit 206, the A-H delay can similarly be communicated to the timing circuit 211 using the communication pathways of the IMD 102.

At 408, a control signal for delivering an electrostimulation at a location that is at or near the His-bundle can be triggered using the A-H delay. For example, the control signal can be triggered by the timing circuit 211, such as after receiving an indication of an onset of a P-wave such as from the detection circuit 210. The control signal can be communicated such as to the electrostimulation energy delivery control circuit 212. The electrostimulation energy delivery control circuit 212 can deliver an electrostimulation such as by using the switching circuit 214, such as for cardiac resynchronization, defibrillation, or the like.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
a timing circuit configured to receive a specified A-H delay, for use for specifying timing between a paced or sensed atrial contraction time (A) and a His-bundle pacing time (H), the specified A-H delay computed using a measured cardiovascular physiologic parameter including at least one of a P-wave duration of an electrical cardiac signal, a parameter of a heart sound signal obtained using a heart sound sensor and indicative of mechanical vibrations of a heart, or a left atrial pressure parameter; and
an electrostimulation energy delivery control circuit configured to be communicatively coupled to the timing circuit and to provide a control signal, in response to a paced or sensed atrial contraction, and using the specified A-H delay, to trigger delivery of an electrostimulation at a location that is at or near the His-bundle.

2. The apparatus of claim 1, comprising a sensor configured to sense an electrocardiogram (ECG) signal, wherein the measured cardiovascular physiologic parameter comprises a P-wave duration measured from the ECG signal.

3. The apparatus of claim 1, comprising a heart sound sensor configured to sense the heart sound signal, wherein the measured cardiovascular physiologic parameter comprises a S1 time of the heart sound signal.

4. The apparatus of claim 1, comprising a blood pressure sensor configured to sense a left atrial pressure signal, wherein the measured cardiovascular physiologic parameter comprises a time of a peak of the left atrial pressure signal.

5. The apparatus of claim 1, wherein the timing circuit is configured to:
receive the measured cardiovascular physiologic parameter; and
compute the specified A-H delay using the received physiologic parameter.

6. The apparatus of claim 5, wherein the measured cardiovascular physiologic parameter comprises a P-wave duration of an electrical cardiac signal, and wherein the timing circuit is configured such that computing the specified A-H delay comprises:
using the P-wave duration; and
using an offset time representative of a delay between the end of the P-wave and a beginning of a QRS complex.

7. The apparatus of claim 6, wherein the timing circuit is configured such that computing the specified A-H delay comprises using, when the paced or sensed atrial contraction is a paced atrial contraction, an A-pace offset time representative of an atrial pacing-atrial sensing differential conduction delay.

8. The apparatus of claim 5, wherein the measured cardiovascular physiologic parameter comprises a S1 time of a heart sound signal, and wherein the timing circuit is configured such that computing the specified A-H delay comprises:
using the S1 time; and
using an offset time representative of a delay between the S1 time and the His-bundle pacing time.

9. The apparatus of claim 8, wherein the timing circuit is configured such that computing the specified A-H delay comprises using, when the paced or sensed atrial contraction is a paced atrial contraction, an A-pace offset time representative of an atrial pacing-atrial sensing differential conduction delay.

* * * * *